United States Patent [19]

Dobbins, III

[11] Patent Number: 4,868,857
[45] Date of Patent: Sep. 19, 1989

[54] VARIABLE COMPENSATION METHOD AND APPARATUS FOR RADIOLOGICAL IMAGES

[75] Inventor: James T. Dobbins, III, Durham, N.C.

[73] Assignee: Duke University, Durham, N.C.

[21] Appl. No.: 114,934

[22] Filed: Oct. 30, 1987

[51] Int. Cl.⁴ .............................................. G01N 23/04
[52] U.S. Cl. ........................................ 378/99; 378/62; 378/159; 358/111
[58] Field of Search ...................... 378/62, 98, 99, 158, 378/159; 358/111; 364/414, 413.23

[56] References Cited

U.S. PATENT DOCUMENTS

| | | | |
|---|---|---|---|
| 3,755,672 | 8/1973 | Edholm et al. | 378/159 |
| 4,322,619 | 3/1982 | Nelson et al. | 378/62 |
| 4,497,062 | 1/1985 | Mistretta et al. | 378/62 |
| 4,636,850 | 1/1987 | Stewart | 358/111 |

Primary Examiner—Carolyn E. Fields
Assistant Examiner—David P. Porta
Attorney, Agent, or Firm—Cushman, Darby & Cushman

[57] ABSTRACT

Method and apparatus for variably compensating a radiographic image irradiates the patient with an x-ray beam. X-ray attenuation (or transmission) variations within the patient are detected and used to modulate the x-ray beam in order to produce an image with equalized exposure and increased SNR. The beam modulation information is used to produce a beam profile image which is an image of the exposure modulation given to the x-ray beam. After the modulated x-ray beam passes through the patient, a compensated image is produced. Both the beam profile image and the compensated image are logarithmically transformed and combined. The logarithmically transformed beam profile image is selectively weighted in order to alter the appearance of the compensated image by various degrees. The combined image is then retransformed and provided to a video monitor for display. An interactive control device controls the amount of weighting to the beam profile image, thus allowing the diagnostician to vary the amount of displayed image compensation desired in the resultant image. The invention produces an image which can be retrospectively adjusted by the diagnostician, or which may be used in either dual-energy imaging systems, or as input in further digital filtering routines.

50 Claims, 6 Drawing Sheets

TRADITIONAL DUAL-ENERGY IMAGING

COMPENSATED DUAL-ENERGY IMAGING

VARIABLE COMPENSATION METHOD AND APPARATUS FOR RADIOLOGICAL IMAGES

BACKGROUND OF THE INVENTION

This invention relates to the field of medical imaging, and particularly to a technique for variably altering the appearance of compensated radiological images, such compensated images being acquired by a device that equalizes the average exposure through different portions of the patient. The present invention allows the diagnostician to optimize an x-ray image by tuning, retrospectively, the amount of dispayed equalization between different portions of the image.

While the present invention will be described in terms of x-ray imaging with respect to chest x-rays, it is to be understood that the teachings of this invention are applicable to a wide range of medical imaging fields.

The field of projection x-ray imaging is well developed and such x-ray equipment is now installed in all hospitals throughout the United States. A problem with known projection x-ray imaging techniques is that the x-ray image transferred to a film recording medium tends to have a great variation in exposure across the image. For example, referring to FIG. 1, a chest x-ray (radiograph) is seen to present widely contrasting light and dark areas. This exposure problem is much like that presented in 35 mm photography, and other imaging systems where the dynamic range of the detecting media (film, etc.) is not as wide as the dynamic range of information available in the imaged object.

In the radiological field, there is often a very wide range of x-ray intensity transmitted through different parts of the patient, particularly radiographic exams such as chest radiographs. This wide variation in transmitted intensity, known as wide dynamic range, leads to degradation of the final image. This degradation occurs because of wide variations of signal-to-noise ratio (SNR) across the image, because of limited film latitude, and because the eye-brain system has a difficult time accommodating wide dynamic ranges.

In recent years, much attention has been given to the optimization of chest radiographs. The chest radiograph is a powerful tool for assessing diseases of the thorax, but it is subject to various physical and perceptual limitations which degrade its diagnostic potential. Two of the main contributors to reduced diagnostic accuracy are large image dynamic range and low lesion conspicuity. Conspicuity is the conspicuousness with which a particular structure appears in the image, compared to the background structure. The large image dynamic range results from the wide disparity in x-ray attenuation between the various structures present in the patient. For example, referring to FIG. 1 it is seen that the lung region is very transmissive to x-rays, while the dense mediastinum areas greatly attenuate x-rays. This is because the mediastinum contains a plurality of structures such as the backbone, aorta, heart, esophagus, bronchial tubes, etc., the whole of which contributes to greater x-ray attenuation than the air-filled lungs. Thus, the chest presents a wide range of x-ray attenuation variations between the lung field and dense regions such as the mediastinum and sub-diaphragmatic areas. The wide range of transmitted and detected x-ray intensity places physical constraints on the imaging system, and also aggravates the psycho-visual process of lesion detection. Poor conspicuity, on the other hand, is the result of the complex network of superposed anatomical structures against which the lesion must be visually discerned. For example, in chest radiographs it is often difficult to discern the presence of small tumors against the mottled background of normal lung structures.

There are three main problems associated with excessive image dynamic range. First, there is a compromised SNR in poorly penetrated regions; it is not uncommon for there to be a 7-fold variation in SNR over the area of a chest radiograph. The problem of reduced SNR in poorly penetrated regions is compounded by the increased contribution of detector noise with large dynamic range. A second problem with large dynamic range is the inability of certain detectors to record the full range of incident intensity. Typical film/screen combinations, for example, do not have sufficient latitude to record the full dynamic range of the chest, resulting in reduced contrast in the poorly penetrated regions. Thirdly, large dynamic range presents display problems since it is difficult to adequately visualize a wide range of image brightnesses simultaneously.

Various approaches have been investigated for eliminating the problems associated with large dynamic range. Generalized procedures such as increasing the kilovoltage of the x-ray source, or using wide-latitude film have been tried, but it is not clear that diagnostic improvement will be achieved since these techniques reduce the contrast of all structures. In addition, digital filtering procedures are also being investigated, but they are limited in their enhancement by the degraded SNR properties of poorly penetrated regions. Various mechanical and photographic techniques have also been tried and have generally yielded improved results. One such technique is a photographic unsharp-masking technique which improves mediastinal nodule detection two-fold. However, this technique also requires fairly extensive film handling and twice the patient exposure. Also, a variety of automated beam filters have been proposed, but many are fairly mechanically cumbersome. Some of these mechanical techniques are generally described in U.S. Pat. No. 3,755,672, to Edholm et al., the teachings of which are also incorporated herein by reference.

Recently, several promising mechanical techniques have been formulated for reducing the dynamic in chest radiography. Notable examples are the Digital Beam Attenuator (DBA), Scanning Equalization Radiography (SER), and the Oldelft Compensator, sometimes known as AMBER (Advanced Multiple Beam Equalization Radiography).

Each of the DBA, SER, and AMBER devices compensates the x-ray beam for perceived x-ray attenuation variations within the object. Briefly, each of these techniques determines the x-ray transmissivity of every point in an object, and then spatially modulates the x-ray beam in accordance with the detected attenuation variations within the object. For example, the DBA technique first takes a low-dose x-ray image of the object. Then, an attenuation filter, or mask, is constructed from the low-dose image in order to reduce the x-ray flux incident on the lung region more than the x-ray flux incident on the mediastinum. For example, the DBA mask (template) may comprise a sheet of paper on which radiation-attenuating materials, such as Cerium Oxide, are imprinted. The DBA mask is then positioned between the object and the x-ray tube, and a second, compensated, image of the object is taken. The compensated image at the detector now has an exposure which is much more uniform across the object, for example see FIG. 3. The DBA technique is more fully describe in U.S. Pat. No. 4,497,062, to Mistretta, et al. (of which the present inventor was a co-inventor), the teachings of which are incorporated herein by reference. In addition, the article "Digital Beam Attenuator Technique for Compensated Chest Radiography", by Hasegawa et al., appearing in Radiology, Vol. 159, Number 2 pp 537-543, 1986, also fully describes the DBA technique, and is also incorporated herein by reference.

The DBA technique is successful at reducing the overall dynamic range in chest radiography, resulting in improved uniformity of image SNR, and improved visualization of mediastinal structures. The DBA technique utilizes 2-dimensional (area) modulation of the incident x-ray beam. This technique provides good temporal resolution since short exposure time (50-100 ms) may be used, during which time patient structures are relatively still. Furthermore, this technique is an efficient use of the x-ray source and reduces x-ray tube loading, resulting in longer tube life and improved reliability. However, two potential difficulties exist with the DBA technique. First, the finite length of time (approximately 50 seconds) required to generate the beam attenuator mask and then place it in the x-ray beam to make the compensated image leads to potential misregistration artifacts between the attenuator mask and the patient. Thus, if the patient moves between generation of the attenuator mask and formation of the compensated image, an inaccurate image will result. This is demonstrated in FIG. 4 where an intentional misregistration between the attenuator and patient was performed to observe the effect. Notice the extreme light and dark areas in the right portion of FIG. 4. Secondly, the DBA technique is mechanically complex, requiring a mechanical printer to print the attenuator mask and a radiation attenuating (for example Cerium Oxide) ribbon for use with the printer. Cerium Oxide ribbons have exhibited a wide range of reliability, thus leading to potential problems with attenuator mask generation.

The SER technique is also a beam compensation technique capable of producing more uniform exposure in a radiological image. In the SER technique, radiation-blocking plates are disposed between the x-ray tube and the patient. One plate has a vertical slot, while the second plate has a horizontal slot, thus providing a pencil-shaped beam of radiation through the overlapping plates. The plates are X-Y driven to produce a x-ray beam raster scan pattern of the pencil beam across the object to be imaged. Behind the object, a feedback detector is located which detects the intensity of x-rays transiting the object. When low x-ray intensity is detected, this indicates a great deal of x-ray attenuation within the object. The feedback detector provides a signal to an x-ray tube modulator which increases the net x-ray flux to compensate for the attenuation within the object. The SER technique is thus a $0^{th}$ dimensional (point) method of beam modulation. The SER modulates the x-ray tube output by changing the length of x-ray pulses, thus requiring a more expensive and complicated x-ray generator and control mechanism. In addition, the SER technique suffers from mechanical complexity from the driving mechanism for the plates in the X-Y direction. Finally, the SER technique demands a great deal of x-ray tube output since only a small portion of the generated x-ray beam actually reaches the object. With replacement x-ray tubes costing approximately $15,000, this technique presents economic disadvantages. The SER technique is more fully described in the articles: "A Scanning Equalization System for Improved Chest Radiology", by Plewes et al. in Radiology, Vol. 142, pp 765-768, 1982; "A Scanning System for Chest Radiography with Regional Exposure Control: Theoretical Considerations", by Plewes in Med. Physics, Vol. 10, pp 646-654, 1983; and "A Scanning System for Chest Radiography with Regional Exposure Control: Practical Implementation", by Plewes et al., in Med Physics, Vol. 10, pp 655-663, 1983, the teachings of which articles are incorporated herein by reference.

The AMBER technique of radiographic compensation is somewhat like the SER technique in that a feedback detector detects x-ray attenuation within the object and then alters the x-ray flux on the object to compensate for x-ray attenuation within the object. The AMBER technique utilizes a plate with a single horizontal slot containing a plurality of vertical occluders therein to attenuate the x-ray beam. The plate produces a plurality of pencil beams which are scanned vertically over the object. Each occluder within the plate includes means for modulating the amount of x-rays passing through that particular position of the slot. There is a feedback detector for each of the pencil beams transiting the object. Each of the feedback detectors is coupled to a respective one of the slot modulating means. As each detector determines the amount of x-ray transmission through the object, it modifies its respective occluder width in order to increase or decrease the amount of x-rays incident on the object. As the x-ray beam scans the object, modulation of the x-ray pencil beams produces various amounts of x-ray intensity in the resultant image. Thus, the AMBER technique is a one-dimensional (line) system of x-ray beam modulation. The AMBER device is believed to have been reduced to practice commercially and is capable of producing usable compensated x-ray images. However, the AMBER technique produces vertical streaking artifacts in the image, between the vertically scanned strips. Moreover, the AMBER technique also makes inefficient use of the x-ray tube since a good portion of the x-ray tube output is blocked by the plate or the slot modulating devices. Again, x-ray tube loading is high. Finally, the AMBER technique is also complicated electrically, requiring the uniformity of response for the plurality of channels (for example, 19 channels) to be carefully coordinated. A more detailed description of the AMBER technique was provided at the Chest Imaging Conference-87 in presentations entitled "Multiple Beam SER System-Technical Aspects of AMBER", by Boelens et al., on Aug. 31, 1987; and "Multiple Beam SER System-Clinical Results", by Ravin on Aug. 31, 1987. Abstracts of both these presentations exist in the Chest Imaging Conference Program, and articles on the presentations are now being prepared, both the articles and their abstracts being also incorporated herein by reference.

In addition, it is expected that future beam compensation techniques will be devised so that exposure equalized radiological images may be provided to diagnosticians. However, all beam compensation devices, present and future, share certain disadvantages. First, in the compensation process eliminates certain large-area information from the image, which information may be diagnostically important. For example, general lung opacity is reduced or eliminated in the compensated image, resulting in potentially degraded diagnosis of large area lung disease. FIG. 3, trace 10 depicts the image signal value across the horizontal midline of the chest. This trace demonstrates that all large area information has been removed from the image, leaving only the small, detailed structures. Secondly, when extreme compensation is carried out considerable edge artifacts (black and white bands) at the heart/lung and diaphragm/lung boundaries may appear. For example, in FIG. 3 it can be seen that certain dark bands exist around the large mediastinal organs. These edge artifacts may prevent accurate diagnosis of phenomena existing in the boundary regions. The reason for such edge artifacts is the high-pass filtration of the x-ray beam from the beam compensation, thus reducing large structure signal while leaving small structure signal intact. The dips in the signal profile in FIG. 3, trace 10 at the edge of the heart are indicative of the edge artifacts from compensation. Thirdly, the beam compensation technique itself may introduce artifacts, such as the vertical streak artifacts produced by AMBER, or the misregistration artifacts produced by the DBA technique. In addition, aggressive compensation in any beam compensation technique may distort the lung images and make a visually "busy" image, resulting in a conspicuity problem in which the background information is confusing and psycho-visual degradation may interfere with the diagnosis. For example, in FIG. 3 the lung areas 16 have been aggressively compensated to make their exposure nearly equal to that of the mediastinum area 18. This may present a busy image and actually interfere with the diagnosis of phenomena in any of the areas. Finally, none of the known or future beam compensation techniques allows for the retrospective alteration of the degree of compensation to fit the specific problem which is the subject of diagnosis. Without the ability to change the degree of compensation, the diagnostician must choose a compromise between improved mediastinal appearance from exposure-equalization, and the degrading effects of edge artifacts and compensator artifacts. Thus, what is needed is a technique which allows the diagnostician to retrospectively alter the degree of displayed compensation in any image in order to choose the exact image best suited to the particular diagnosis being considered.

Thus, what is needed is a reliable, inexpensive system adaptable for use with any beam compensation technique which allows the diagnostician to retrospectively alter the degree of displayed image compensation while maintaining the other, beneficial aspects of compensation techniques.

SUMMARY OF THE INVENTION

The variable compensation technique was developed to address the above-discussed problems by allowing the clinician to interactively and retrospectively adjust the amount of displayed image compensation. The amount of displayed compensation is adjusted by retroactively adding back into the compensated image some portion of the spatial modulation applied to the incident x-ray beam. The representation of the incident beam modulation is discussed herein as a beam profile image, but may be embodied as a signal matrix or signal stream related to the modulation of the incident x-ray beam. For example, the variable compensation technique discussed herein permits high compensation to be selected for improved mediastinal visibility, and low compensation to be selected for assessment of large structures, such as the lungs. The present technique also permits the viewer to determine if a visual anomaly is an edge artifact by selecting a zero-compensation appearance (thereby simulating the appearance of a traditional chest image). A truly unique and significant aspect of this technique is that image SNR does not change appreciably with increasing amounts of displayed compensation. This result is contrary to that typically experienced with traditional post-acquisition digital filtering routines.

Briefly, the variable compensation technique uses an x-ray beam modulator to compensate the x-ray image for the detected variations of x-ray transmission through the object. The beam modulator spatially modulates the incident beam in accordance with the detected variations in beam transmission through the object. A beam profile image is obtained which is related to the amount of beam modulation introduced into the x-ray beam in order to compensate for the x-ray attenuation variations. A compensated image of the object is also produced by allowing the modulated x-ray beam to pass through the object. A logarithmic transformation is taken of both the beam profile image and the compensated image. The log of the beam profile image is then weighted in order to effect compensation adjustment. The weighting is accomplished by an interactive control operated by the diagnostician. The weighted, log beam profile image is then added subtrated from the log of the compensated image in order to produce the final image. This final image is then subjected to a re-exponentiation process to produce an output image with suitable appearance. The digital signal from the output image may then be transformed into an analog signal for display at a monitor. Preferably, a hard copy (film) device is coupled to the monitor for producing a hard copy of the variably compensated image. Thus, the diagnostician views the image on the monitor and then adjusts the interactive control to produce the desired amount of displayed compensation appearance. This process is done retrospectively since the object was only subjected to a single (or at most two) radiation scans. The images are stored in computer memory and may be selectively recalled for weighting and adjustment to produce the desired amount of displayed compensation in the resultant image.

The present invention proposes both method and apparatus for carrying out the operations discussed above. Specifically, this disclosure teaches a method of variably compensating an x-ray image of an object including the steps of (a) directing an x-ray beam through an object such as a patient, (b) detecting the x-ray attenuation (or transmission) variations in the object (c) compensating the x-ray beam for the detected x-ray attenuation (or transmission) variations in the object, (d) producing a beam profile image in accordance with the resulting x-ray beam modulation variations incident on the object, (e) producing a compensated image of the object from the modulated x-ray beam passing through the object, (f) variably weighting the beam profile image, and (g) combining the compensated image with the weighted beam profile image to produce a variably compensated x-ray image of the object.

The present invention also proposes apparatus for variably compensating an x-ray image of an object, including (a) an x-ray source for directing an x-ray beam through the object, (b) a beam compensator device, positioned between the x-ray source and the object, for compensating the x-ray beam for x-ray attenuation (or transmission) variations detected in the object, (c) a detector device for producing a beam profile image from the modulated x-ray beam, (d) a detector device for producing a compensated image from the modulated x-ray beam passing through the object, (e) a processor for adding some portion of the beam profile image to the compensated image to produce a variably compensated image, and (f) interactive control apparatus for weighting the beam profile image in accordance with the desires of the operator.

BRIEF DESCRIPTION OF THE DRAWINGS

The advantageous structure and method according to the present invention will be more clearly understood from the following detailed description of the presently preferred exemplary embodiments, when taken together with the attached drawings which show.

DETAILED DESCRIPTION OF THE PRESENTLY PREFERRED EXEMPLARY EMBODIMENTS

Figure 4:
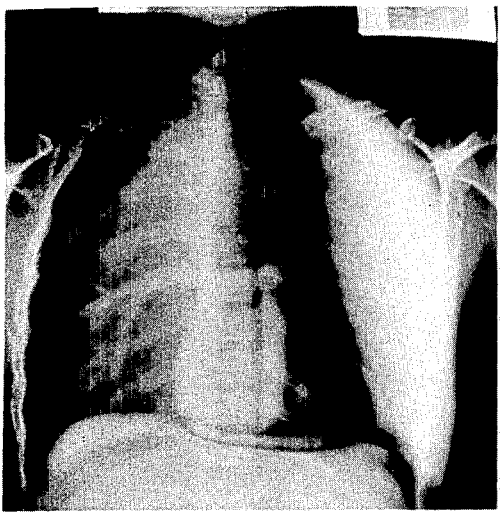
FIG. 4 depicts a DBA compensated image showing misregistration artifacts.
Figure 5:
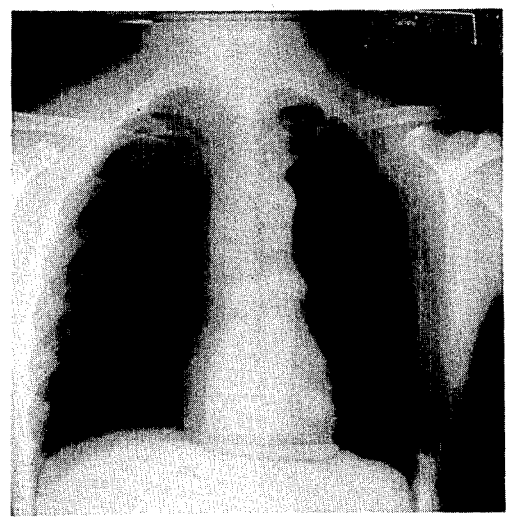
FIG. 5 depicts a variably compensated image showing zero-degree of displayed compensation with removal of DBA misregistration artifacts.

The variable compensation technique combines the high SNR of beam compensation with the flexibility of interactively-selectible spatial-frequency response. This goal is achieved by combining the compensated image with the known beam compensator modulation information from the beam profile image. A number of important advantages are inherent in the variable compensation process For example, it is envisioned that the variable compensation process will be carried out digitally which allows adding back in a degree of displayed dynamic range, retrospectively. Thus, only a single (or at most two) images must be acquired in order for the diagnostician to generate a potentially infinite number of variously-compensated images. Since the beam compensator equalized the exposure in the original image, the SNR of all variable compensation images is still very good, and is much better in the dense patient regions than in a non-compensated x-ray image. Thus, variable compensation allows image alteration while retaining the superior SNR characteristics of beam compensation techniques. In addition, large area information can be added back into the final image, by degrees, so that diagnostic information in all areas of the patient are not lost. The variable compensation technique allows large area information to be eliminated or restored by mere adjustment of a variable control. Also, edge artifacts may be reduced or eliminated by using interactive control to simulate images with small amounts of displayed compensation. Also, artifacts introduced by specific beam compensation techniques may be removed by adjustment of the interactive control to give a small amount of displayed compensation. For example, DBA misregistration artifacts depicted in FIG. 4 may be eliminated by the variable compensation technique, as shown in FIG. 5. Finally, the variable compensation technique will enhance the commercial appeal of all beam compensation devices because of the enhanced diagnostic information available to the clinician.

As presently envisioned, the variable compensation technique can be utilized in three specific ways. First, compensated x-ray images of a patient can be taken and then retrospectively and interactively adjusted to vary the degree of displayed compensation in accordance with the requirements of the diagnosis. Secondly, a compensated x-ray image of a patient may be taken and then rendered with a very low degree of displayed compensation (like in FIG. 1), and then introduced to known or proposed digital filtering algorithms in order to accomplish further image processing. Those of skill in the medical imaging field understand that a wide variety of digital image processing techniques are known and proposed for improving radiological images. A variable compensation image with zero compensation appearance would be a unique candidate for such digital processing techniques since the image retains good SNR, while preserving the normal visual appearance most commonly used with digital processing. Thirdly, a low-compensation variable compensation image with small compensation appearance may be obtained and utilized in the known Dual Energy Imaging (DEI) technique.

Figure 10:
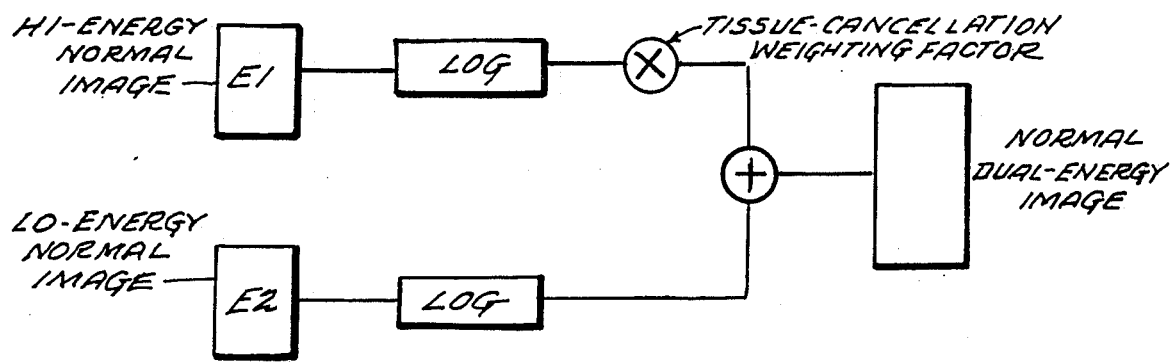
FIG. 10 depicts the generalized, prior art dual-energy imaging technique.

Dual Energy Imaging (variously known as Dual-Energy, Energy-Subtraction, or Tissue-cancellation imaging) is an imaging technique which permits x-ray images to be generated that contain only anatomical structures of one particular tissue type. For example, an image of the chest could be generated that contained only calcified tissues (such as ribs, spine, and calcified nodules). Alternatively, an image could be generated that contained only soft-tissue structures (where the bones have been made to disappear). The technique works by acquiring two x-ray images, each at a different beam energy, and then forming a linear combination of the logarithm of these two images, see FIG. 10. Soft-tissue or bone may be made to disappear in the resulting image by exploiting the known difference in energy-dependence of the attenuation coefficients of bone and soft-tissue when performing the linear combination. A brief summary of the mathematics for Dual-Energy Imaging will now be presented. First, a normal x-ray image containing bone and soft-tissue may be written as:

$$I = I_0 \cdot \exp(-\mu_t t_t - \mu_b t_b) \tag{1}$$

where the $\mu$'s are attenuation coefficients, and $t_t$ and $t_b$ are soft-tissue and bone thicknesses respectively. If one takes two images, one at an energy E1 and another at an energy E2, then the logarithms of the images may be written as follows:

$$L_1 = -t_1 t_t - \mu_{b1} t_b + k_1 \quad (2)$$

$$L_2 = -\mu_{t2} t_t \mu_{b2} + k_2 \quad (3)$$

A dual-energy image is formed by taking a linear combination of images $L_1$ and $L_2$ as follows:

$$L = L_1 + \beta \cdot L_2 = -t_t(\mu_{t1} + \beta \cdot \mu_{t2}) - t_b(\mu_{b1} + \beta \cdot \mu_{b2}) + k \quad (4)$$

The coefficient $\beta$ determines the particular tissue to be cancelled. For example, to cancel soft-tissue, $\beta W_{t1}/\mu_{t2}$, to cancel bone, $\beta = N_{b1}/\mu_{b2}$. Making the bone term equal to zero actually leaves a negative imprint of the bone, so it is actually necessary to make soft-tissue and bone appear identical to make the bones vanish. The dual-energy technique has been known in the literature for several decades, and has been investigated for a variety of imaging tasks. For example, a good description of the dual-energy technique is given in Chapter 6 of the present Inventor's PhD dissertation entitled "Multiple-Energy Tissue-Cancellation Applications of a Digital Beam Attenuator to Chest Radiography", by Dobbins, University of Wisconsin-Madison, April 1985, the teachings of which are incorporated herein by reference.

The dual-energy technique has demonstrated the ability to render images with good tissue cancellation, despite the many physical processes which could potentially degrade the images. There has not been widespread acceptance of the dual-energy technique in clinical practice, however, for several reasons. The first reason is the lack of suitable large area digital detector, which limitation has been greatly reduced by the recent advent of photostimulable phosphor detectors and various scanning detectors. A second and more fundamental difficulty with dual-energy imaging has been the degraded image SNR present in the tissue-cancelled images. This has been particularly true of images with soft-tissue cancellation. However, since the variable compensation technique according to the present invention can reduce SNR degradation, the variable compensation technique is especially suited to improve dual-energy techniques.

The primary reason for the SNR degradation in dual-energy imaging is the loss of signal amplitude incumbent with the dual-energy mathematical algorithm. In equation (4) it can be seen that when the soft-tissue cancellation condition is applied, the soft-tissue coefficient goes to zero. However, the effective bone coefficient is also greatly diminished. In combination with the frequently poor quantum statistics in the high-energy beam, the loss of signal amplitude always leads to a loss of SNR when performing dual-energy imaging. In practice, this loss of SNR has only been troublesome in the very poorly penetrated regions of anatomy, such as the mediastinum, where the SNR is normally low to begin with. Generally, the lungs have not experienced an unacceptable SNR in dual-energy imaging due to the excellent SNR originally present in these areas of high photon transmittance. As a result, soft-tissue cancelled images are typically poor in the mediastinum, making the detection of calcified lesions near the mediastinum difficult.

The variable compensation technique offers an excellent way to improve the SNR in the mediastinum for use in dual-energy imaging. The particular adaptation of variable compensation techniques to dual-energy imaging will be provided later herein with reference to FIG. 11.

As an overview to the variable compensation technique, the initial step is to determine the x-ray attenuation variations in the patient, and hence the amount of x-ray beam modulation required for compensation. This may be accomplished by taking a first low-dose image, or by monitoring feedback signals from an x-ray beam modulator, or by providing a detector between the x-ray tube and the object in order to detect only the modulated x-ray beam. The representation of the x-ray beam modulation is utilized to generate a beam profile image which represents the modulated x-ray beam prior to its passing through the patient. Then, a very aggressively compensated image of the object (with excellent SNR) is obtained by allowing the modulated x-ray beam to pass through the object to a detector. After logarithmically transforming both images, the beam profile image may be weighted with a variable weighting function. The transformed, compensated image is then altered by subtracting from it a fractionally weighted amount of the transformed, beam profile image to add back various amounts of image dynamic range subtracted out during the compensation process. The weighting may be changed interactively while viewing the displayed image on a video monitor.

Figure 7:
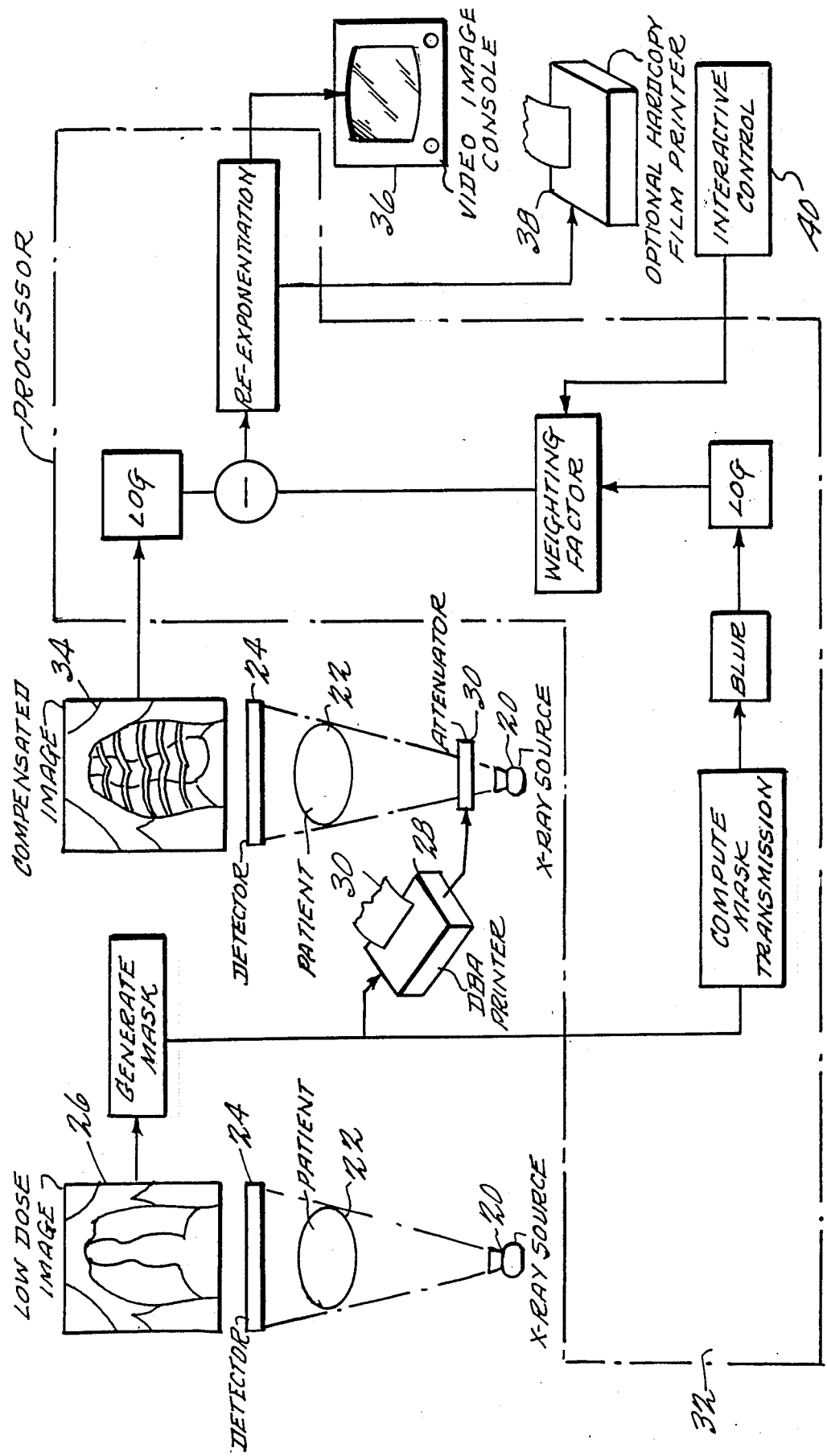
FIG. 7 depicts apparatus for carrying out variable compensation with the DBA technique.

FIG. 7 depicts one apparatus which may be used to accomplish variable compensation with the DBA beam compensation technique. In FIG. 7, a first low-dose image of the patient is taken to generate the DBA mask. X-ray source 20 irradiates patient 22 with a low exposure of x-rays. The x-rays passing through patient 22 impinge on detector 24 and produce an image 26 of the patient. Note that detector 24 may be film, a digital photoelectronic detector, or any other known or equivalent means of detecting x-rays.

Next, the low-dose image 26 is used to generate a DBA mask for later use in producing the compensated image. For example, the DBA mask may be generated by DBA printer 28 which is a dot-matrix printer having a Cerium-Oxide ribbon to imprint a negative of low-dose image 26 on paper 30. Cerium-Oxide is a known x-ray attenuator. The amount of attenuation to be given to any particular portion of paper 30 is determined by the number of times the Cerium-Oxide ribbon is printed onto paper 30. For example, a great deal of Cerium-Oxide will be printed in the lung region, while very little Cerium-Oxide will be printed over the mediastinum area.

Consecutively with preparing the DBA mask, a digital representation of the negative of low-dose image 26 is also provided to processor 32. Processor 32 utilizes this digital information to compute the mask transmission properties of the DBA mask. The DBA mask transmission image then comprises the beam profile image which is later utilized to alter the compensated appearance of the compensated image in a variable manner. The beam profile image thus represents the amount of modulation given to the x-ray beam to compensate it for the x-ray attenuation variations within patient 22.

Figure 3:
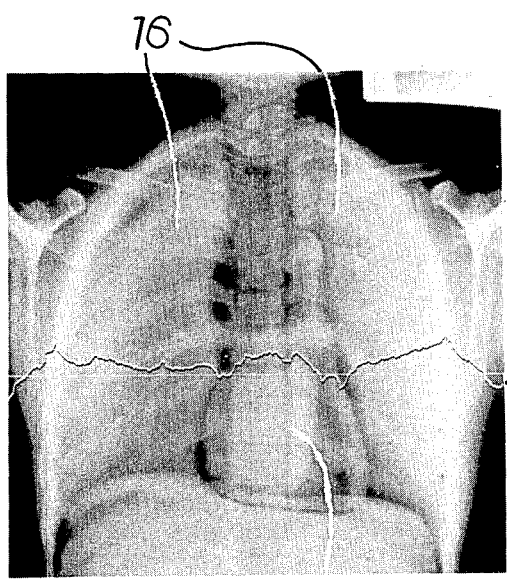
FIG. 3 depicts a variably compensated image with a 100 percent degree of displayed compensation.

As a next step, a second image of the patient is made with the DBA mask (attenuator 30 interposed between x-ray source 20 and patient 22. Detector 24 now produces a compensated image 34 in which the amount of exposure across the image is equalized. Such an image is depicted in FIG. 3 and is known as an aggressively compensated image, one in which 100% of the compensation appearance is maintained. This is one extreme of a variably compensated image. Note in FIG. 3 that the image signal trace 10 across the entire chest image is fairly level.

Figure 6:
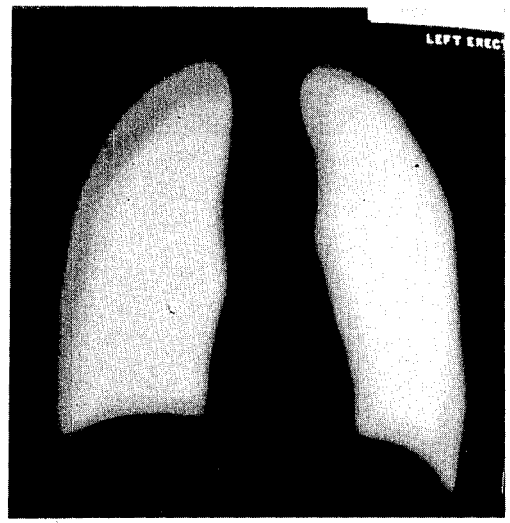
FIG. 6 depicts a blurred beam profile image.

The digitized compensated image 34 is then passed to processor 32 which also contains the beam profile image derived from the DBA mask transmission. Inside processor 32, the DBA-compensated image 34 is then logarithmically transformed. At the same time, the beam profile image obtained from the calculated mask transmission is also logarithmically transformed. An additional blurring may be performed on the beam profile image in order to improve the noise properties of the beam profile image, and also to match the blurring of the mask from the x-ray tube focal spot. FIG. 6 depicts such a blurred beam profile image. Note that the lung areas are light, denoting aggressive x-ray beam attenuation, while the mediastinal areas appear dark, denoting little x-ray attenuation. After logarithmic transformation of both images, a weighting factor may be applied to the transfomed beam profile image in order to subtract fractional amounts thereof from the compensated image. After subtraction of the images, the resulting image is re-exponentiated, converted to an analog signal, and provided to a video image console 36. In addition, an output may be provided to the optional hard copy printer 38, which, for example, may be a film printer. Interactive control 40 is used to adjust the weighting factor of the beam profile image.

Mathematically, the general variable compensation technique will be described below. A normal x-ray image may be described as follows:

$$I(x,y) = I_0 \cdot T_p(x,y) \tag{5}$$

where $T_p$ is the patient transmission, $I_0$ is the radiation intensity incident on the patient, and I is the detected image intensity. An image compensated with any beam compensator may be described as follows:

$$I_{comp}(x,y) = I_0 \cdot T_c(x,y) \cdot T_p(x,y) \tag{6}$$

Figure 1:
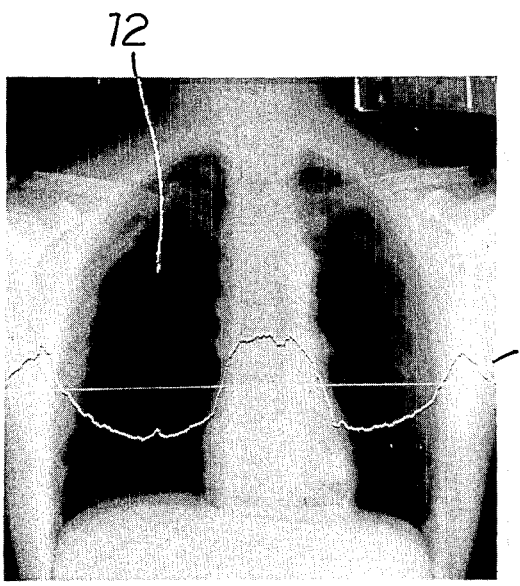
FIG. 1 depicts a variably compensated image, with a zero-degree of displayed compensation.

$T_c$ is the spatial transmission function of the beam compensator, and $I_{comp}$ is the image intensity in the compensated image. With the variable compensation technique, it is desired to modify the appearance of the compensated image from the extremes of a completely compensated appearance (FIG. 3) to a completely uncompensated appearance (FIG. 1). To achieve this retrospective image modification, an exponential factor $\alpha$ is introduced and will be used to divide out varying amounts of beam compensation transmission:

$$I_{vc}(x,y) = [I_{comp}(x,y)]/[\{T_c(x,y)\}^\alpha] \tag{7}$$

where $T'_c$ denotes the estimated beam compensator transmission, and $I_{vc}$ is the resulting variable compensation image intensity. It should be noted that when $\alpha=0$, the result is $I_{vc}=I_{comp}$, and when $\alpha=1$, the result is $I_{vc}=I$ (uncompensated appearance). In order to simplify the computations, we shall logarithmically transform the images:

$$L_{vc} = L_{comp} - \alpha \cdot \ln(T_c) \tag{8}$$

Note that the image $L_{comp}$ is just the logarithm of the compensated image. The function $T_c$, may be obtained from the beam profile image as follows:

$$I_{bp} = I_0 \cdot T_c' \tag{9}$$

which after logarithmic transformation gives:

$$\ln(T_c) = L_{bp} + k \tag{10}$$

where k equals a constant and $L_{bp}$ is the logarith of the beam profile image. Therefore, equation (8) becomes:

$$L_{vc} = L_{comp} - \alpha \cdot L_{bp} + k' \tag{11}$$

where the variable compensated image here expressed in terms of the beam profile image and the compensated image. To obtain the variably compensated image $I_{vc}$, one simply re-exponentiates $L_{vc}$.

These digital manipulations, may be performed in software, or alternatively with real-time digital look-up tables (LUT's), and arithmetic logic units (ALU's) for instantaneous interactive control. Initial investigations utilized a VAX 11/780 for processor 32. However, such a slow processor does not provide real-time imaging, requiring a few seconds between modification of the weighting factor and display of the resultant image.

Figure 2:
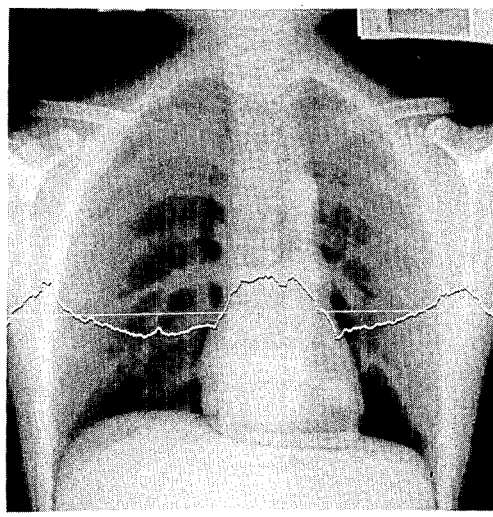
FIG. 2 depicts a variably compensated image with a moderate degree of displayed compensation.

Interactive control device 40 alters weighting factor $\alpha$ in order to effect various degrees of displayed compensation. Interactive control 40 may be implemented as a control knob, a keyboard, or a preset number of keys. For example, one key may provide a zero weighting factor (FIG. 3), a second button may provide a 50% weighting factor (FIG. 2), while a third button would provide a 100% weighting factor (FIG. 1). Those with skill in this field will recognized that any known and convenient way of effecting weighting control may be utilized.

The blurring of the beam profile image carried out in processor 32 is advantageous in order to ensure adequate SNR, and also to mimic the blurring of the actual attenuator in the x-ray beam from the x-ray tube focal spot, (see FIG. 6).

In operation, the variably compensated image is presented on monitor 36 to the clinician. The clinician then views the variably compensated image and retrospectively alters the amount of displayed compensation at the console. The physician then may select the amount of displayed compensation which displays most favorably the anatomy of interest. This technique not only permits selective enhancement of various anatomic regions, but also permits the viewing clinician to distinguish the presence of edge-artifacts and compensation-specific artifacts. The resulting image still has superb SNR at all points and may be subjected to digital post-processing routines if image enhancement is desired.

Figure 8:
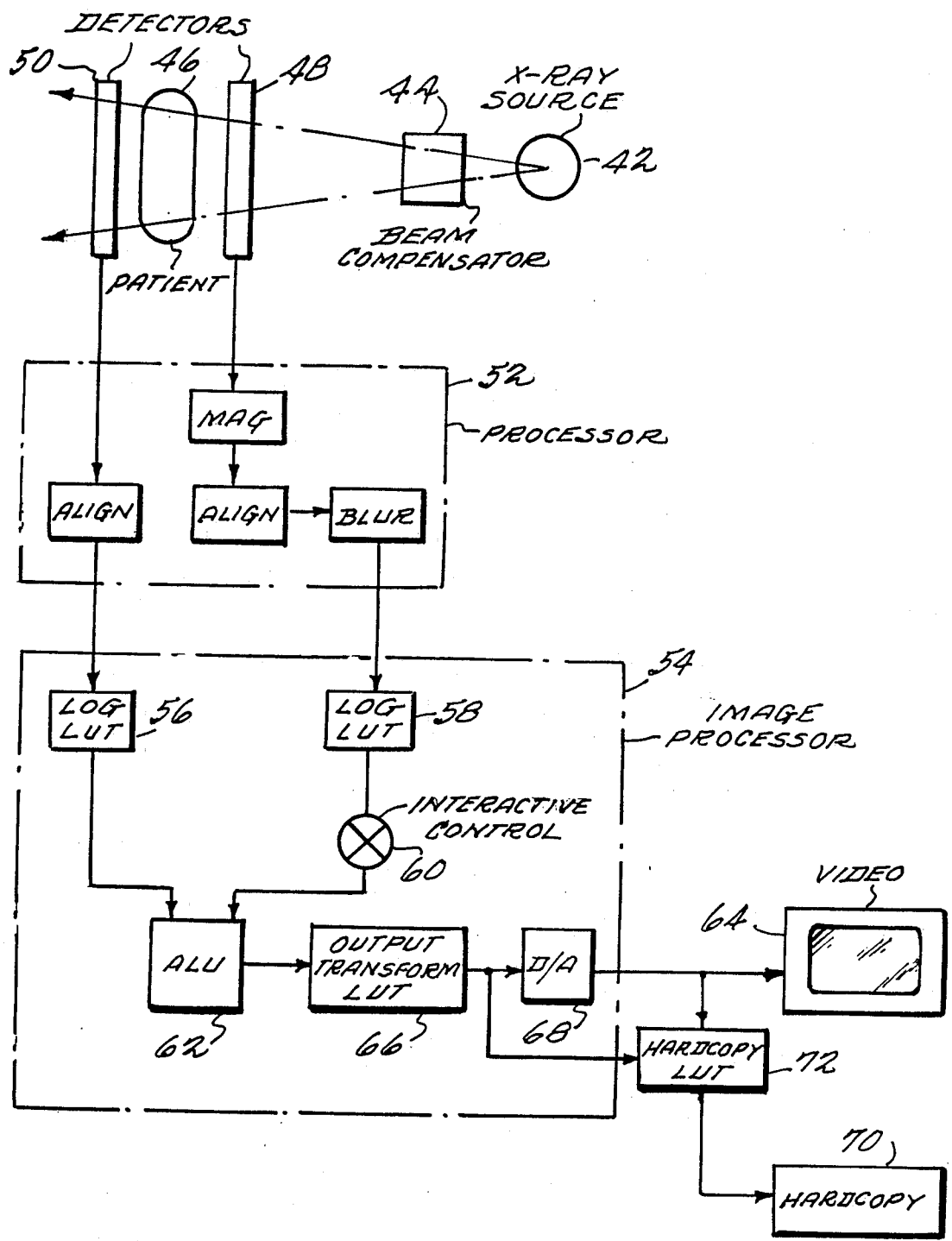
FIG. 8 depicts apparatus for carrying out variable compensation, usable with any beam compensation technique.

FIG. 8 depicts an embodiment of the present invention which would be usable with any known or projected method of beam compensation. In FIG. 8, x-ray source 42 provides an x-ray beam to beam compensator 44. Beam compensator 44 may be a DBA mask, a SER compensator, an AMBER compensator, or any other known or envisioned beam compensation device. Beam compensator 44 thus produces an x-ray beam which has been modulated to compensate for x-ray attenuation variations in patient 46.

The compensated x-ray beam first strikes upstream (upbeam) detector 48 to produce the beam profile image. Then, the compensated x-ray beam penetrates patient 46 and is detected by downstream (downbeam) detector 50. This produces the compensated image.

Both the beam profile image and the compensated image are provided to a general processor 52 which, for example, may be a VAX 11/780. Within the general processor 52, the beam profile image is first magnified to take into account the beam spread between upstream detector 48 and downstream detector 50. Next, processor 52 will align the beam profile image with the compensated image to ensure proper registration in the final output image. Lastly, processor 52 will blur the beam profile image to improve the SNR, as discussed above.

The compensated image and the beam profile image are then provided to an image processor 54, which may be a Gould IP9516 image processor. Image processor 54 uses logarithmic LUT's 56 and 58 to logarithmically transform the beam profile image and the compensated image.

Interactive control 60 may be an integral part of processor 54, or a separate device coupled thereto. Interactive control device 60 is used to weight the logarithmically transformed beam profile image in order to vary the displayed variable compensation in the resulting image.

The transformed compensated image, and the weighted, transformed beam profile image are then provided to Arithmetic Logic Unit (ALU) 62. Arithmetic Logic Unit 62 combines the compensated image with the weighted beam profile image in order to produce the resultant image viewable on video monitor 64.

After combining the images, ALU 62 provides the resultant image to output transform LUT 66. This look-up table retransforms the resultant image back into a normal range of image values. The resulting image is then passed to digital-to-analog converter 68 which outputs an analog signal to video monitor 64 for viewing purposes.

The output of image processor 54 may also be provided to a hardcopy device 70 which may produce a hardcopy (film, printed paper, etc.) of the resultant image. Optionally, a hardcopy LUT 72 may be provided in order to produce a media-specific modification of the resultant image. For example, hardcopy LUT 72 may contain information regarding the different film speeds which may be used in hardcopy device 70.

Figure 9:
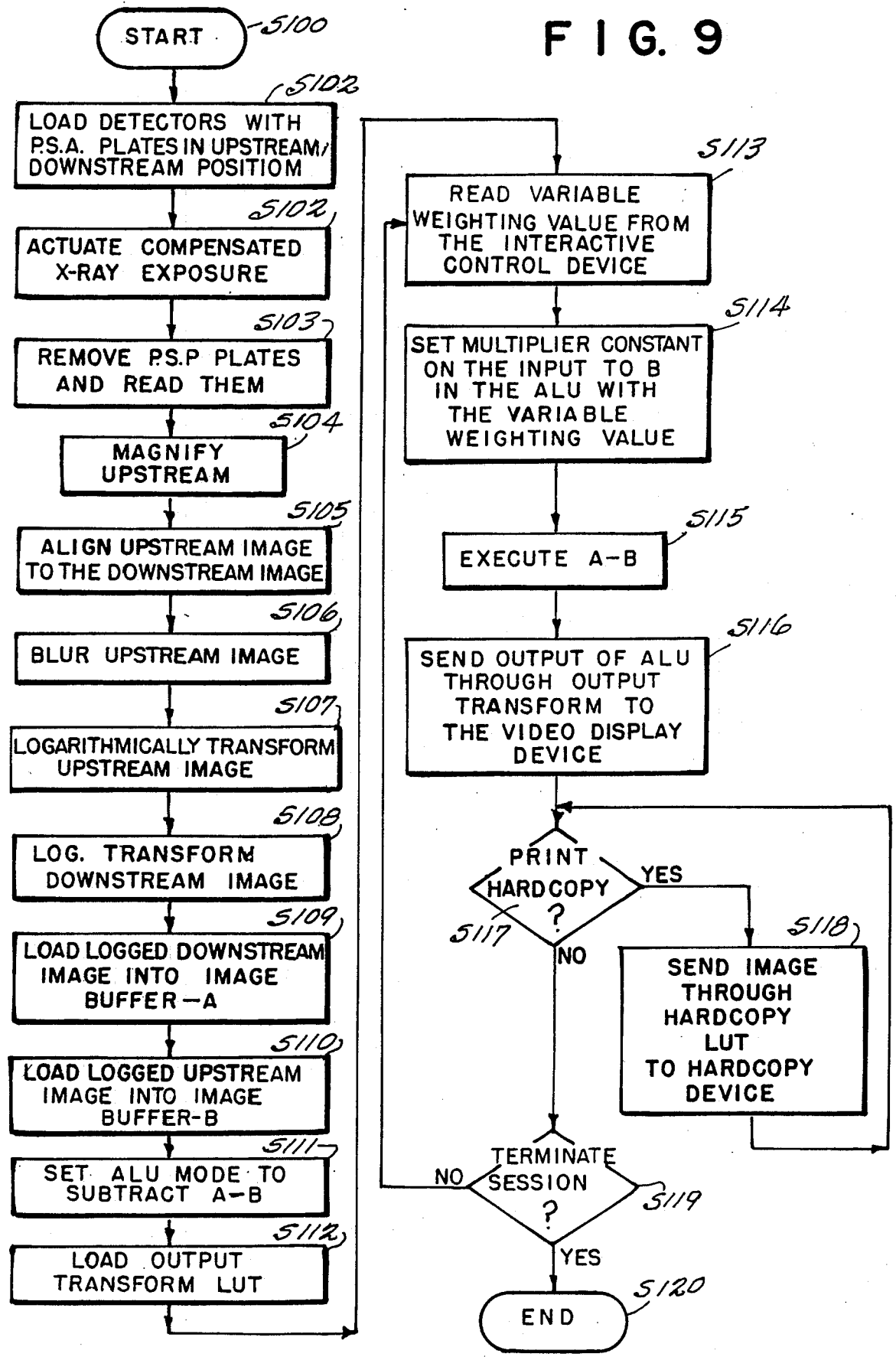
FIG. 9 depicts a process, top-level flow chart for performing the functions of the apparatus depicted in FIG. 8.

FIG. 9 depicts a top-level process flowchart for carrying out variable compensation with the apparatus according to FIG. 8. In FIG. 9, the process starts at step S100 with initialization of the processors. At step S101 upstream detector 48 and downstream detector 50 are loaded with photostimulable phosphor plates. At step S102, x-ray source 42 and beam compensator 44 are activated and x-ray images are produced on upstream detector 48 and downstream detector 50.

Step S103 requires the removal of the photostimulable phosphor plates from each of the detectors, and the reading of information from the plates to processor 52. At step S104, the beam profile image from upstream detector 48 is magnified. Then, at step S105, the compensated image and the beam profile image are aligned with respect to each other. At step S106, the beam profile image is blurred.

Step S107 logarithmically transforms the beam profile image, while step S108 logarithmically transforms the compensated image. The logged compensated image is then loaded into an image buffer A, at step S109. Likewise, at step S110 the logged beam profile image is loaded into image buffer B. At step S111, the mode of ALU 62 is set to subtract buffer B from buffer A.

At step S112, output transform LUT 66 is loaded. Then, at step S113, the variable weighting value from interactive control 60 is read. At step S114, the multiplier constant on the input of ALU 62 from interactive device 60 is set with the variable weighting value read from interactive control device 60.

The execution of the arithmetic operation A-B is next carried out in ALU 62, as shown in step S115. At step S116, the output of ALU 62 is provided through output transform LUT 66, and D/A 68, to video display device 64. At step S117 it is determined whether a hardcopy print-out is required. If yes, the image is sent through hardcopy LUT 72 to hardcopy device 70, as indicated in step S118. The process then returns to step S117. If a hardcopy is not requested, it is determined whether the session should be terminated at step S119. If a further change in the displayed compensation of the resultant image is required, the process returns to step S113. If the session is to be terminated, the process proceeds to end step S120.

Figure 11:
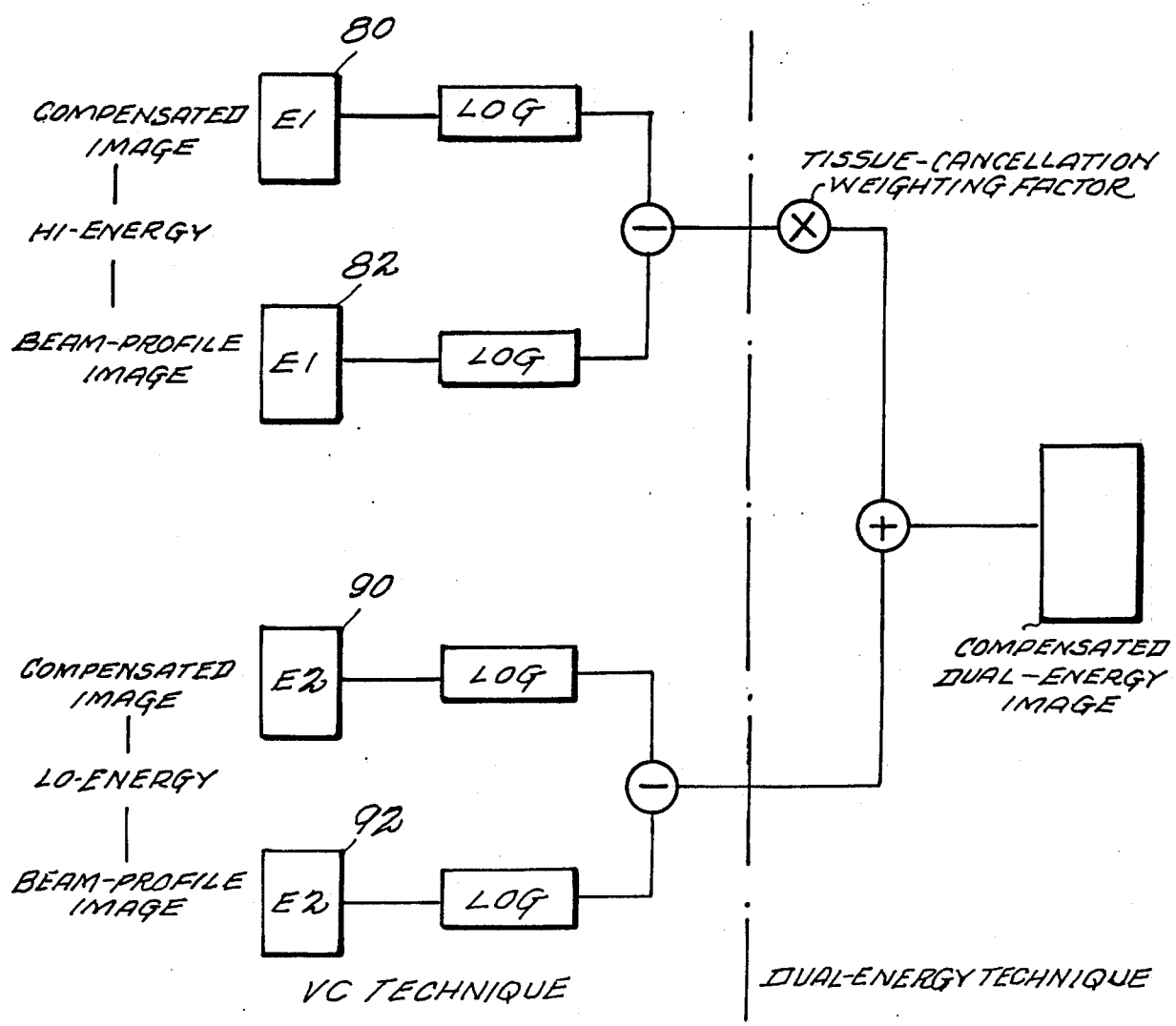
FIG. 11 depicts the adaptation of the variable compensation technique to the dual-energy imaging technique.

Thus, what has been described above is one of the uses of the variable compensation technique, to provide variable amounts of displayed compensation to a resultant image after beam compensation techniques have been applied. As mentioned above, another use of the variable compensation technique is with dual-energy imaging. Such a use is depicted in FIG. 11. As discussed above, the variable compensation technique offers an excellent way to improve the SNR in the mediastinum in dual-energy images. Recall that the variable compensation technique uses an x-ray beam compensator to equalize the photon flux reaching the detector at all points by forcing larger amounts of radiation through the denser regions of the patient. Hence, the beam compensator forces an improvement in inherent SNR in the dense regions, such as the mediastinum, due to the improved quantum statistics. However, the use of a beam compensator may result in large shading artifacts in dual-energy images, since the dual-energy algorithm does not anticipate the spatial alteration of the x-ray beam from the beam compensator. The variable compensation technique may be used to eliminate the offending shading artifacts by subtracting the visual presence of the beam compensator from the compensated images prior to using the dual energy technique. Stated another way, the variable compensation technique may be used prior to the dual-energy technique to provide both high-energy and low-energy images with improved mediastinal SNR (from the beam compensator) but with the same image appearance as the corresponding uncompensated images. The dual-energy technique would then introduce no shading artifacts since the high and low-energy images have normal appearance. Turning to FIG. 11, the application of the variable compensation technique to the dual energy technique is depicted. First, a high-energy compensated image 80 and a high-energy beam profile image 82 are obtained. Both images are logarithmically transformed and the beam profile image is subtracted from the compensated image. In this particular application, it is envisioned that an image with zero-degree of compensation appearance (see FIG. 1) will result from the subtraction of the beam profile image from the fully compensated image. Thus, the high-energy portion of the dual-energy technique will produce a high-energy, zero compensation appearance image.

The low-energy portion of the variable compensation/dual-energy technique first produces a low-energy compensated image 90 and a low-energy beam profile image 92. Both images are logarithmically transformed and the beam profile image is subtracted from the compensated image to also produce a zero compensated appearance image of the object. Next, a tissue-cancellation weighting factor may be applied to the high-energy variable-compensation image in order to cancel appropriate tissue (either soft-tissue or bone). The weighted high-energy variable compensation image is then added to the low-energy variable compensation image to produce a compensated dual-energy image with high SNR and with the appropriate tissue cancelled out. Thus, the combination of the variable compensation technique with the dual-energy technique provides the diagnostician with an additional tool to properly diagnose a patient.

The third use of the variable compensation technique mentioned above is the use of a variably compensated image as input to further digital processing or filtering routines. Since digital filtering and processing is extremely varied, concrete examples are not provided herein. Suffice it to say that the variable compensation technique provides a unique resource to improve the image input to digital processing and imaging routines. The variable compensation technique can provide an image with a high SNR and a variable degree of displayed compensation so that many digital processing and imaging routines can be used on the image for a wide variety of purposes.

In summary, the variable compensation technique may be utilized to provide input to digital processing routines; to expand the use of dual-energy imaging techniques; and to permit the viewing of high SNR images with varying degrees of compensated appearance. The technique permits the viewing clinician to change the amount of displayed compensation retrospectively to selectively enhance various portions of patient anatomy. This is done at a viewing monitor roughly in real-time with an interactive control. Films with desired amounts of compensation may then be printed (as with a laser printer) for later viewing at a viewbox if desired. The variable compensation technique also reduces or eliminates edge-enhancement artifacts or compensator-specific artifacts from the image. The variable compensation technique may be used to verify if an object is an edge-artifact or anatomical structure by reducing the apparent compensation. Also, the variable compensation technique may be used to give a simulated zero-compensation appearance, which would have the appearance of an uncompensated image but with high SNR.

Various embodiments of viewing consoles and interactive display mechanisms are possible. A preferred embodiment would probably be a small box next to the viewing console, with a lever or knob that may be actuated to increase or decrease the apparent amount of compensation. This box could serve as an interface with the image processor which would alter the relative weighting of the blurred beam profile image. An alternative embodiment would be to give the clinician a set of buttons on the computer console which would alter the image appearance. Also, the particular digital detector used to acquire the chest images with this technique is not pertinent to the concept disclosed herein, but may effect the actual embodiment. Any number of digital detectors may be used, such as photostimulable phosphor detectors (marketed by Philips and Fuji), scanning digital detectors (such as a device marketed by Picker), large-area photodetector arrays (still being developed), large-area image intensifiers, or large-area, flat-plate intensifiers (such as those investigated at Duke University). Lastly, the actual software algorithms used to form the image blurrings and combinations with the variable compensation technique are dependent on the type of image display device used. A dumb display (frame buffer) would require all of the blurrings, weightings, and combinations to be done in software and then would display the final result. A more preferable embodiment is to use a multiple-frame display with an arithmetic logic unit which can perform the weightings and combinations roughly in real-time. Regardless of the actual embodiment constructed, the variable compensation technique discussed herein provides a unique tool to the field of medical imaging, and especially to medical radiography.

Thus, what has been described is method and apparatus for variably compensating the exposure of a radiographic image for the variations in x-ray attenuating structure within a patient. The variable compensation technique will provide a unique tool to medical imagers and will advance the art of medical imaging by stimulating further development in radiological imaging systems.

I claim:

1. A method of compensating an image of an x-ray beam incident on an object, comprising the steps of:
   beam compensating an x-ray beam to produce an object-incident x-ray beam;
   producing a beam profile image indicative of a distribution of x-ray flux into said object by said object-incident x-ray beam;
   producing a compensated image of said object indicative of an amount of said x-ray flux from said object-incident x-ray beam exiting said object; and
   combining at least a portion of said beam profile image with said compensated image.

2. A method according to claim 1 wherein said step of producing the beam profile image includes the steps of:
   directing an x-ray beam through said object;
   detecting x-ray attenuation variations in said object from said x-ray beam passing through said object; and
   generating said beam profile image in accordance with the detected x-ray attenuation variations in said object.

3. A method according to claim 2 wherein said generating step includes the step of producing a DBA mask.

4. A method according to claim 2 wherein said generating step includes the steps of positioning an upstream detector upbeam of said object.

5. A method according to claim 2 wherein said generating step includes the steps of:
   directing an x-ray beam, which has been modulated for the detected x-ray attenuation variations in said object, toward said object; and
   detecting the modulated x-ray beam before it reaches said object.

6. A method according to claim 1 wherein said combining step includes the step of combining a variable portion of said beam profile image with said compensated image.

7. A method of compensating an x-ray image of an object, comprising the steps of:
   directing an x-ray beam through said object;
   detecting x-ray attenuation variations in said object;
   modulating said x-ray beam based on the detected x-ray attenuation variations in said object;

producing a beam profile image in accordance with the modulated x-ray beam incident on said object;

producing a compensated image of said object from the modulated x-ray beam passing through said object;

weighting said beam profile image; and combining said compensated image with the weighted beam profile image to produce a compensated x-ray image of said object.

8. A method according to claim 7 wherein said step of producing a beam profile image includes the steps of:

generating a DBA mask from the detected x-ray attenuation variations in said object;

computing a mask transmission image of said DBA mask; and logarithmically transforming said mask transmission image.

9. A method according to claim 8 wherein the step of producing the compensated image includes the steps of:

detecting the modulated x-ray beam passing through said object;

constructing a detected compensated image from the detected modulated x-ray beam passing through said object; and logarithmically transforming the detected compensated image.

10. A method according to claim 9 wherein said weighting step includes the step of weighting the logarithmically transformed mask transmission image.

11. A method according to claim 7 wherein said step of producing a beam profile image includes the steps of:

positioning an upstream detector upbeam of said object;

detecting the modulated x-ray beam prior to its reaching said object; and generating said beam profile image in accordance with the detected modulated x-ray beam.

12. A method according to claim 11 wherein said generating step includes the step of logarithmically transforming said beam profile image.

13. A method according to claim 12 wherein said weighting step includes the step of weighting the logarithmically transformed beam profile image.

14. A method according to claim 13 wherein the step of producing the compensated image includes the steps of:

detecting the modulated x-ray beam passing through said object;

constructing a detected compensated image from the detected modulated x-ray beam passing through said object; and logarithmically transforming the detected compensated image.

15. A method according to claim 14 wherein said combining step includes the step of combining the logarithmically transformed compensated image with the weighted, logarithmically transformed beam profile image.

16. A method according to claim 7 wherein the compensating step includes the step of DBA compensation of said x-ray beam.

17. A method according to claim 7 wherein the compensating step includes the step of SER compensating said x-ray beam.

18. A method according to claim 7 wherein the compensating step includes the step of AMBER compensating said x-ray beam.

19. A method according to claim 7 wherein said step of producing a beam profile image includes the step of blurring said beam profile image.

20. A method of producing a compensated radiological image of an object, comprising the steps of:

directing an x-ray radiation beam through said object;

modulating said radiation beam for radiation attenuation variations in said object;

producing signals representing a beam profile image corresponding to the modulated radiation beam;

producing signals representing a compensated image corresponding to the modulated radiation beam after it passes through said object;

logarithmically transforming the signals representing both the beam profile image and the compensated image;

weighting the logarithmically transformed signals representing the beam profile image;

combining the weighted, logarithmically transformed signals representing the beam profile image with the logarithmically transformed signals representing the compensated image;

retransforming the combined signals; and outputting the retransformed signals as output signals representing a compensated radiological image.

21. A method according to claim 20 wherein said weighting step includes the step of selectively choosing one of a plurality of weighting levels.

22. A method according to claim 20 further including the steps of:

blurring those signals representing said beam profile image; and aligning the blurred beam profile signals with the signals representing the compensated image.

23. A method according to claim 20 further including the step of displaying the compensated radiological image.

24. A method according to claim 20 further including the step of producing a hard copy of said compensated radiological image.

25. Apparatus for compensating an x-ray image of an object, comprising:

means for producing a beam profile image indicative of a distribution of a flux of a beam-compensated x-ray beam, into said object;

means for producing a compensated image of said object based on an amount of said flux of said beam-compensated x-ray beam exiting said object; and means for combining at least a portion of said beam profile image with said compensated image.

26. Apparatus according to claim 25 wherein said means for producing a beam profile image includes:

means for directing an x-ray beam through said object;

means for detecting x-ray attenuation variations in said object from said x-ray beam passing through said object; and means for generating said beam profile image in accordance with the detected x-ray attenuation variations in said object.

27. Apparatus according to claim 26 wherein said generating means includes means for producing a DBA mask.

28. Apparatus according to claim 26 wherein said generating means includes an upstream detector positioned upbeam of said object.

29. Apparatus according to claim 26 wherein said means for generating includes:
   means for directing an x-ray beam, which has been modulated for the detected x-ray attenuation variations in said object, toward said object; and
   means for detecting the modulated x-ray beam before it reaches said object.

30. Apparatus according to claim 25 wherein said means for combining includes means for varying that portion of said beam profile image which is combined with said compensated image.

31. Apparatus for compensating an x-ray image of an object, comprising:
   means for directing an x-ray beam through said object;
   means for detecting x-ray attenuation variations in said object;
   means for modulating said x-ray beam for the detected x-ray attenuation variations in said object;
   means for producing a beam profile image in accordance with the modulated x-ray beam incident on said object;
   means for producing a compensated image of said object from the modulated x-ray beam passing through said object;
   means for weighing said beam profile image; and
   means for combining said compensated image with the weighted beam profile image to produce a compensated x-ray image of said object.

32. Apparatus according to claim 31 wherein said means for producing a beam profile image includes:
   means for generating a DBA mask from the detected x-ray attenuation variations in said object;
   means for computing a mask transmission image of said DBA mask; and
   means for logarithmically transforming said mask transmission image.

33. Apparatus according to claim 32 wherein said means for producing the compensated image includes:
   means for detecting the modulated x-ray beam passing through said object;
   means for constructing a detected compensated image from the detected modulated x-ray beam passing through said object; and
   means for logarithmically transforming the detected compensated image.

34. Apparatus according to claim 33 wherein said means for weighting includes means for variably weighting the logarithmically transformed mask transmission image.

35. Apparatus according to claim 31 wherein said means for producing a beam profile image includes;
   upstream detector means positioned upbeam of said object;
   means for detecting said modulated x-ray beam prior to its reaching said object;
   means for generating said beam profile image in accordance with the detected modulated x-ray beam.

36. Apparatus according to claim 35 wherein said means for generating includes means for logarithmically transforming said beam profile image.

37. Apparatus according to claim 36 wherein said weighting means includes means for weighting the logarithmically transformed beam profile image.

38. Apparatus according to claim 37 wherein said means for producing the compensated image includes:
   downstream detector means positioned down beam of said object for detecting the modulated x-ray beam passing through said object;
   means for constructing a detected compensated image from the detected modulated x-ray beam passing through said object; and
   means for logarithmically transforming the detected compensated image.

39. Apparatus according to claim 38 wherein said means for combining includes means for combining the logarithmically transformed compensated image with the weighted, logarithmically transformed beam profile image.

40. Apparatus according to claim 31 wherein said means for compensating includes means for DBA compensating said x-ray beam.

41. Apparatus according to claim 31 wherein said means for compensating includes means for SER compensating said x-ray beam.

42. Apparatus according to claim 31 wherein said means for compensating includes means for AMBER compensating said x-ray beam.

43. Apparatus according to claim 31 wherein said means for producing a beam profile image includes means for blurring said beam profile image.

44. Apparatus for producing a compensated radiological image of an object comprising:
   means for directing an x-ray radiation beam through said object;
   means for modulating said radiation beam for radiation attenuation variations in said object;
   means for producing signals representing a beam profile image corresponding to the modulated radiation beam;
   means for producing signals representing a compensated image corresponding to the compensated radiation beam after it passes through said object;
   processor means for (a) logarithmically transforming the signals representing both the beam profile image and the compensated image, (b) weighting the logarithmically transformed signals representing the beam profile image, (c) combining the weighted, logarithmically transformed signals representing the beam profile image with the logarithmically transformed signals representing the compensated image, (d) retransforming the combined signals, and (e) outputting the retransformed signals as output signals representing a compensated radiological image.

45. Apparatus according to claim 44 further including means for selectively choosing one of a plurality of weighting levels in said procesor means.

46. Apparatus according to claim 44 further including:
   means for blurring those signals representing said beam profile image, and aligning the blurred beam profile signals with the signals representing the compensated image.

47. Apparatus according to claim 44 further including means for displaying the compensated radiological image.

48. Apparatus according to claim 44 further including means for producing a hard copy of said compensated radiological image.

49. Apparatus for compensating an x-ray image of an object, comprising:
   x-ray source means for directing an x-ray beam through said object;

compensator means, positioned between said x-ray source means and said object, for modulating said x-ray beam for x-ray attenuation variations in said object;

upstream detector means, positioned between said compensator means and said object, for producing a beam profile image from the modulated x-ray beam;

downstream detector means, positioned on an opposite side of said object from said upstream detector means, for producing a compensated image from the modulated x-ray beam passing through said object; and processor means, coupled to said upstream and said downstream detector means, for combining at least a portion of said beam profile image with said compensated image to produce a resultant compensated image.

50. Apparatus according to claim 49 further including means for selectively weighting the beam profile image to vary the apparent compensation of said compensated image.

* * * * *

UNITED STATES PATENT AND TRADEMARK OFFICE
CERTIFICATE OF CORRECTION

PATENT NO. : 4,868,857
DATED : September 19, 1989
INVENTOR(S) : DOBBINS, III It is certified that error appears in the above-identified patent and that said Letters Patent is hereby corrected as shown below:

In column 1, line 6, before "This" insert

--This invention was made with Government support under Grant No. CA 43854 awarded by the National Institutes of Health. The Government has certain rights in the invention.--

Signed and Sealed this

Eighteenth Day of April, 1995

Attest:

BRUCE LEHMAN

*Attesting Officer*

*Commissioner of Patents and Trademarks*